United States Patent [19]

Shutske

[11] Patent Number: 4,806,646

[45] Date of Patent: Feb. 21, 1989

[54] SUBSTITUTED 9-AMINO-SPIRO[CYCLOALKYL[B]QUINO-LINE-2,1'CYCLOALKANES]

[75] Inventor: Gregory M. Shutske, Somerset, N.J.

[73] Assignee: Hoechst-Roussel Pharmaceuticals, Inc., Somerville, N.J.

[21] Appl. No.: 192,037

[22] Filed: May 9, 1988

Related U.S. Application Data

[62] Division of Ser. No. 31,825, Mar. 30, 1987, Pat. No. 4,762,841.

[51] Int. Cl.$^4$ .................. C07D 221/20; A61K 31/435
[52] U.S. Cl. ........................ 546/15; 560/35; 562/440; 314/278
[58] Field of Search .......................... 546/15

[56] References Cited

U.S. PATENT DOCUMENTS 4,631,286 12/1986 Shutske et al. .................. 514/297

FOREIGN PATENT DOCUMENTS 0268871 6/1988 European Pat. Off. .

Primary Examiner—Robert T. Bond
Attorney, Agent, or Firm—Tatsuya Ikeda

[57] ABSTRACT

There are disclosed compounds having the formula

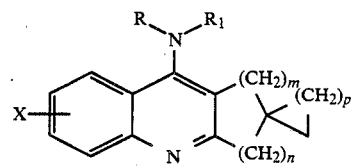

wherein m is 1 or 2; n is 1 or 2; p is 1–5; x is hydrogen, loweralkyl, cycloalkyl, loweralkoxy, halogen, hydroxy, nitro, trifluoromethyl, formyl, loweralkylcarbonyl, arylcarbonyl, —SH, loweralkylthio, —NHCOR$_2$ or —NR$_3$R$_4$ where R$_2$ is hydrogen or loweralkyl, and R$_3$ and R$_4$ are independently hydrogen, loweralkyl or cycloalkyl; R is hydrogen, loweralkyl or loweralkylcarbonyl; and R$_1$ is hydrogen, loweralkyl, loweralkylcarbonyl, aryl, diloweralkylaminoloweralkyl, arylloweralkyl, diarylloweralkyl, oxygen-bridged arylloweralkyl or oxygen-bridged diarylloweralkyl; stereo, optical and geometrical isomers thereof, and pharmaceutically acceptable acid addition salts thereof, which are useful for enhancing memory.

1 Claim, No Drawings

SUBSTITUTED 9-AMINO-SPIRO[CYCLOALKYL[B]QUINOLINE-2,1'CYCLOALKANES]

This is a division, of co-pending application Ser. No. 031,825, filed Mar. 30, 1987, now U.S. Pat. No. 4,762,841.

This invention relates to compounds having the formula

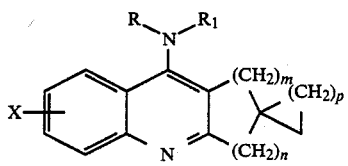

wherein m is 1 or 2; n is 1 or 2; p is 1–5; X is hydrogen, loweralkyl, cycloalkyl, loweralkoxy, halogen, hydroxy, nitro, trifluoromethyl, formyl, loweralkylcarbonyl, arylcarbonyl, —SH, loweralkylthio, —NHCOR$_2$ or —NR$_3$R$_4$ where R$_2$ is hydrogen or loweralkyl, and R$_3$ and R$_4$ are independently hydrogen, loweralkyl or cycloalkyl; R is hydrogen, loweralkyl or loweralkylcarbonyl; and R$_1$ is hydrogen, loweralkyl, loweralkylcarbonyl, aryl, diloweralkylaminoloweralkyl, arylloweralkyl, diarylloweralkyl, oxygen-bridged arylloweralkyl or oxygen-bridged diarylloweralkyl; stereo, optical and geometrical isomers thereof, which are useful for enhancing memory, methods for synthesizing them, and pharmaceutical compositions comprising an effective memory enhancing amount of such a compound, and a method of increasing the cholinergic function in mammals which comprises the administration of an effective amount of such a compound.

This invention also relates to compounds having the formulas

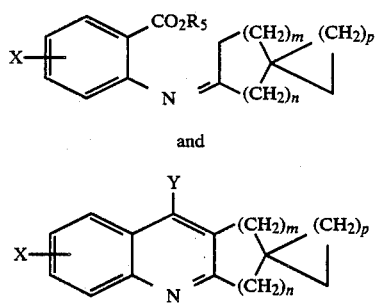

wherein X, m, n, and p are as defined above, R$_5$ is hydrogen or loweralkyl, and Y is halogen, hydroxy or loweralkoxy, which are useful as intermediates for synthesizing the compounds of Formula I.

Throughout the specification and the appended claims, a given chemical formula or name shall encompass all stereo, optical and geometrical isomers thereof where such isomers exist, as well as pharmaceutically acceptable acid addition salts thereof and solvates thereof such as for instance hydrates.

The following definitions shall apply throughout the specification and the appended claims.

Unless otherwise stated or indicated, the term loweralkyl denotes a straight or branched alkyl group having from 1 to 6 carbon atoms. Examples of said alkyl include methyl, ethyl, n-propyl, iso-butyl, pentyl, and hexyl.

Unless otherwise stated or indicated, the term cycloalkyl denotes a saturated ring containing 3 to 7 carbon atoms. Examples of said cycloalkyl include cyclopropyl, cyclohexyl and cycloheptyl.

Unless otherwise stated or indicated, the term loweralkoxy denotes a straight or branched alkoxy group having 1 to 6 carbon atoms. Examples of said loweralkoxy include methoxy, ethoxy iso-propoxy, sec-butoxy and straight and branched chain hexyloxy.

Unless otherwise stated or indicated, the term halogen shall mean fluorine, chlorine, bromine or iodine.

Unless otherwise stated or indicated, the term aryl shall mean an unsubstituted phenyl group or a phenyl group substituted with 1, 2 or 3 substituents each of which being independently loweralkyl, loweralkoxy, halogen, hydroxy, trifluoromethyl phenoxy or benzyloxy.

Unless otherwise stated or indicated, the term oxygen-bridged shall signify the fact than an oxygen atom is present between aryl and loweralkyl groups and/or an oxygen atom has replaced a methylene group in the lowerakyl group, with the proviso that said methylene group is not alpha to the amino nitrogen carrying the groups R and R$_1$. Thus, for instance, examples of oxygen-bridged arylloweralkyl include 3-phenoxypropyl and 4-phenoxybutyl, and examples of oxygen-bridged diarylloweralkyl include 2-[bis(4-fluorophenyl)methoxy]ethyl and 2-[bis(3-fluorophenyl)methoxy]ethyl.

The compounds of this invention are prepared by utilizing one or more of the steps described below.

In order to simplify the description of the synthetic schemes, the description will be presented with specific reference to the situation where m=1, n=2 and p=3, but it will readily be understood that the synthetic schemes can also be applied to the other situations by making obvious modifications where necessary.

Throughout the description of the synthetic steps, the definitions of X, Y, R and R$_1$ through R$_5$ are as given above unless otherwise stated or indicated.

STEP A

A compound of formula IIa can be prepared by reacting a compound of Formula IV with spiro[4.5]decan-7-one. Said reaction can be conducted in a suitable solvent such as benzene, toluene or xylene at a temperature of about 80°–150° C. in the presence of an acid catalyst such as p-toluene sulfonic acid, benzenesulfonic acid or methanesulfonic acid.

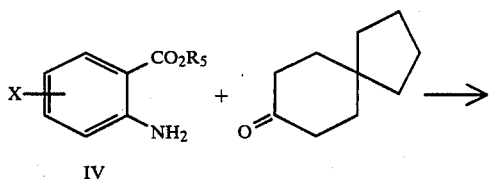

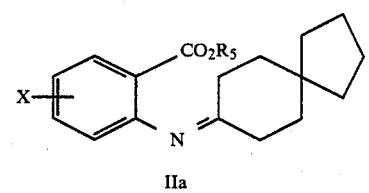

STEP B

A compound of Formula IIIa can be prepared by reacting compound IIa with phosphorous pentoxide in the presence of a high boiling tertiary amine such as N,N-dimethylcyclohexylamine. Said reaction can be conducted without additional solvent at a temperature of about 170°-220° C.

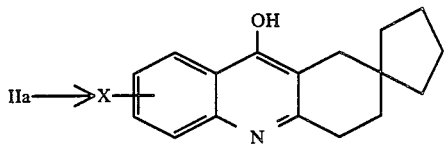

IIIa

STEP C

A compound of Formula IIIb can be prepared by reacting compound IIIa with phosphorous oxychloride and phosphorous pentachloride. Said reaction can be conducted at a temperature of about 100°-150° C.

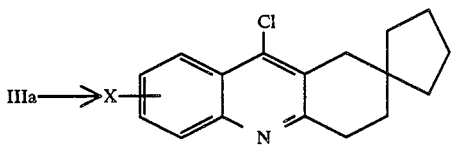

IIIb

The bromine analogue of compound IIIb can be prepared in a similar manner, namely, for instance by reacting compound IIIa with phosphorous oxybromide and phosphorous pentabromide. The fluorine and iodine analogues of compound IIIa can be prepared by replacing the chlorine atom of compound IIIa with fluorine or iodine in a routine manner known to the art.

STEP D

A compound of Formula VI can be prepared by reacting compound IIIb with an amine of formula V. Said reaction can be conducted at a temperature of 120°-220° C. in the presence of a hydroxylated aromatic compound such as or phenol or cresol.

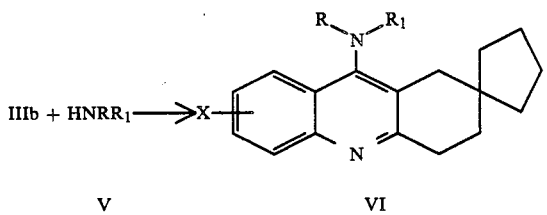

V        VI

Steps A through D can be combined into a single step. Thus compound VI can be obtained by heating together a mixture of phosphorous pentoxide, N,N-dimethylcyclohexylamine and the hydrochloride of maine V and then adding compound IV followed by spiro[5.5]undecan-3-one. Said reaction can be carried out at a temperature of 150°-250° C.

STEP E

A compound of Formula VIa can be prepared by reacting an anthranilonitrile of Formula VII with spiro[4.5]decan-7-one. Said reaction can be conducted in the presence of a Lewis acid such as zinc chloride, without solvent at a temperature of about 80°-150° C. or in a solvent such as 1,2-dichloroethane or nitrobenzene, again at a temperature of about 80°-150°.

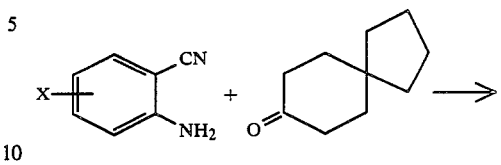

VII

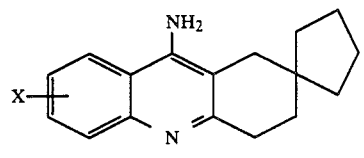

VIa

The compounds of Formula I of the present invention can be used for the treatment of various memory dysfunctions characterized by decreased cholinergic function, such as Alzheimer's disease.

This utility can be ascertained by determining the ability of these compounds to inhibit the activity of the enzyme acetylcholinesterase and thereby increase the acetylcholine levels in the brain.

This utility can also be ascertained by determining the ability of these compounds to restore cholinergically deficient memory in the Dark Avoidance Assay. In this assay mice are tested for their ability to remember an unpleasant stimulus for a period of 24 hours. A mouse is placed in a chamber that contains a dark compartment; a srong incandescent light drives it to the dark compartment, where an electric shock is administered through metal plates on the floor. The animal is removed from the testing apparatus and tested again, 24 hours later, for the ability to remember the electric shock.

If scopolamine, an anticholinergic that is known to cause memory impairment, is administered before an animal's initial exposure to the test chamber, the animal re-enters the dark compartment shortly after being placed in the test chamber 24 hours later. This effect of scopolamine is blocked by an active test compound, resulting in a greater interval before re-entry into the dark compartment.

Effective quantities of the compounds of the invention may be administered to a patient by any of the various methods, for example, orally as in capsules or tablets parenterally in the form of sterile solutions or suspensions, and in some cases intravenously in the form of sterile solutions. The free base final products, while effective themselves, may be formulated and administered in the form of their pharmaceutically acceptable acid addition salts for purposes of stability, convenience of crystallization, increased solubility and the like.

Acids useful for preparing the pharmaceutically acceptable acid addition salts of the invention include inorganic acids such as hydrochloric, hydrobromic, sulfuric, nitric, phosphoric and perchloric acids, as well as organic acids such as tartaric, citric, acetic, succinic, maleic, fumaric and oxalic acids.

The active compounds of the present invention may be orally administered, for example, with an inert diluent or with an edible carrier, or they may be enclosed in gelatin capsules, or they may be compressed into tablets. For the purpose of oral therapeutic administration, the active compounds of the invention may be incorporated with excipients and used in the form of tablets, troches, capsules, elixirs, suspensions, syrups, wafers, chewing gum and the like. These preparations should contain at least 0.5% of active compound, but may be varied depending upon the particular form and may conveniently be between 4% to about 70% of the weight of the unit. The amount of active compound in such compositions is such that a suitable dosage will be obtained. Preferred compositions and preparations according to the present invention are prepared so that an oral dosage unit form contains between 1.0–300 milligrams of active compound.

The tablets, pills, capsules, troches and the like may also contain the following ingredients: a binder such as micro-crystalline cellulose, gum tragacanth or gelatin; an excipient such as starch or lactose, a disintegrating agent such as alginic acid, Primogel, cornstarch and the like; a lubricant such as magnesium stearate or Sterotex; a glidant such as colloidal silicon dioxide; and a sweetening agent such as sucrose or saccharin may be added or a flavoring agent such as peppermint, methyl salicylate, or orange flavoring. When the dosage unit form is a capsule, it may contain, in addition to materials of the above type, a liquid carrier such as a fatty oil. Other dosage unit forms may contain other various materials which modify the physical form of the dosage unit, for example, as coatings. Thus tablets or pills may be coated with sugar, shellac, or other enteric coating agents. A syrup may contain, in addition to the active compounds, sucrose as a sweetening agent and certain preservatives, dyes, coloring and flavors. Materials used in preparing these various compositions should be pharmaceutically pure and non-toxic in the amounts used.

For the purpose of parenteral therapeutic administration, the active compounds of the invention may be incorporated into a solution or suspension. These preparations should contain at least 0.1% of active compound, but may be varied between 0.5 and about 30% of the weight thereof. The amount of active compound in such compositions is such that a suitable dosage will be obtained. Preferred compositions and preparations according to the present invention are prepared so that a parenteral dosage unit contains between 0.5 to 100 milligrams of active compound.

The solutions or suspensions may also include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates citrates or phosphates and agents for the adjustment of tonicity such as sodium chloride or dextrose. The parenteral preparations can be enclosed in disposable syringes or multiple dose vials made of glass or plastic.

Examples of the compounds of this invention include:
9-amino-3,4-dihydrospiro[acridine-2(1H),1'-cyclopropane];
9-amino-3,4-dihydro-6-trifluoromethylspiro[acridine-2(1H),1'-cyclopropane];
3,4-dihydro-9-methylaminospiro[acridine-2(1H),1'-cyclopropane];
9-benzylamino-3,4-dihydrospiro[acridine-2(1H),1'-cyclopropane];
9-benzylamino-7-chloro-3,4-dihydrospiro[acridine-2(1H),1'-cyclopropane];
9-anilino-3,4-dihydrospiro[acridine-2(1H),1'-cyclopropane];
9-amino-3,4-dihydrospiro[acridine-2(1H),1'-cyclopentane];
9-amino-6-chloro-3,4-dihydrospiro[acridine-2(1H),1'-cyclopentane];
9-amino-3,4-dihydro-6-methoxyspiro[acridine-2(1H),1'-cyclopentane];
3,4-dihydro-9-methylaminospiro[acridine-2(1H),1'-cyclopentane];
3,4-dihydro-6-fluoro-9-methylaminospiro[acridine-2(1H),1'cyclopentane];
9-(4-chlorobenzylamino)-3,4-dihydrospiro[acridine-2(1H),1'-cyclopentane];
9-anilino-3,4-dihydrospiro[acridine-2(1H),1'-cyclopentane];
3,4-dihydro-9-(2-fluoroanilino)spiro[acridine-2(1H),1'-cyclopentane];
9-amino-3,4-dihydrospiro[acridine-2(1H),1'-cyclohexane];
7-acetamido-9-amino-3,4-dihydrospiro[acridine-2(1H),1'-cyclohexane];
9-amino-3,4-dihydro-7-methoxyspiro[acridine-2(1H)1'-cyclohexane];
7-chloro-3,4-dihydro-9-methylaminospiro[acridine-2(1H),1'-cyclohexane];
3,4-dihydro-9-(3-fluorobenzylamino)spiro[acridine-2(1H),1'-cyclohexane];
3,4-dihydro-9-(3-methoxybenzylamino)spiro[acridine-2(1H),1'-cyclohexane];
3,4-dihydro-9-(4-methoxyanilino)spiro[acridine-2(1H),1'-cyclohexane];
9-amino-1,3-dihydrospiro[cyclopenta[b]quinoline-2,1'-cyclopentane];
9-amino-1,3-dihydro-6-fluorospiro[cyclopenta[b]quinoline-2,1'-cyclopentane];
9-amino-1,3-dihydro-7-methoxyspiro[cyclopenta[b]quinoline-2,1'-cyclopentane];
7-acetamido-9-amino-1,3-dihydrospiro[cyclopenta[b]quinoline-2,1'-cyclopentane];
1,3-dihydro-9-methylaminospiro[cyclopenta[b]quinoline-2,1'-cyclopentane];
1,3-dihydro-9-propylaminospiro[cyclopenta[b]quinoline-2,1'-cyclopentane];
1,3-dihydro-9-(4-methylbenzylamino)spiro[cyclopenta[b]quinoline-2,1'-cyclopentane];
9-(3,4-dichlorobenzylamino)-1,3-dihydrospiro[cyclopenta[b]quinoline-2,1'-cyclopentane];
9-(3,4-dichloroanilino)-1,3-dihydrospiro[cyclopenta[b]quinoline-2,1'-cyclopentane];
9-amino-1,3-dihydrospiro[cyclopenta[b]quinoline-2,1'-cyclohexane];
1,3-dihydro-9-ethylaminospiro[cyclopenta[b]quinoline-2,1'-cyclohexane];
9-benzylamino-1,3-dihydrospiro[cyclopenta[b]quinoline-2,1'cyclohexane]; and
9-anilino-1,3-dihydrospiro[cyclopenta[b]quinoline-2,1'-cyclohexane].

I claim:
1. A compound having the formula

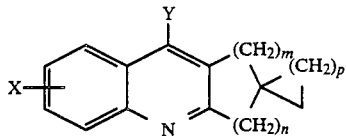
wherein m is 1 or 2; n is 1 or 2; p is 1–5; X is hydrogen, loweralkyl, cycloalkyl, loweralkoxy, halogen, hydroxy, nitro, trifluoromethyl, formyl, loweralkylcarbonyl, arylcarbonyl, —SH, loweralkylthio, —NHCOR$_2$ or —NR$_3$R$_4$ where R$_2$ is hydrogen or loweralkyl, and R$_3$ and R$_4$ are independently hydrogen, loweralkyl or cycloalkyl; and Y is halogen, hydroxy or loweralkoxy.
* * * * *